United States Patent [19]

Crossman et al.

[11] Patent Number: 5,100,427
[45] Date of Patent: Mar. 31, 1992

[54] DISPOSABLE LANCET DEVICE

[75] Inventors: David D. Crossman, Watlington; Jeremy Marshall, Jericho, both of Great Britain

[73] Assignee: Owen Mumford Limited, Oxford, Great Britain

[21] Appl. No.: 604,462

[22] Filed: Oct. 29, 1990

[30] Foreign Application Priority Data

Nov. 4, 1989 [GB] United Kingdom ............... 8924937

[51] Int. Cl.5 ........................................... A61B 17/32
[52] U.S. Cl. ...................................................... 606/182
[58] Field of Search ............... 606/182, 181; 604/136, 604/110, 157; 128/770

[56] References Cited

U.S. PATENT DOCUMENTS

| 4,139,011 | 2/1979 | Benoit et al. ............... 606/182 |
| 4,230,118 | 10/1980 | Holman et al. ............ 606/182 |
| 4,375,815 | 3/1983 | Burns ........................ 606/182 |
| 4,379,456 | 4/1983 | Cornell et al. ............. 606/182 |
| 4,388,925 | 7/1983 | Burns ........................ 606/182 |
| 4,416,279 | 11/1983 | Lindner et al. ............ 606/182 |
| 4,517,978 | 5/1985 | Levin et al. ............... 606/182 |
| 4,527,561 | 7/1985 | Burns ........................ 606/182 |
| 4,715,374 | 12/1987 | Maggio ...................... 606/182 |
| 4,817,603 | 4/1989 | Turner et al. .............. 606/182 |
| 4,856,515 | 8/1989 | Turner et al. .............. 606/182 |
| 4,895,147 | 1/1990 | Bodicky et al. ............ 606/182 |

FOREIGN PATENT DOCUMENTS

| 0061102 | 9/1982 | European Pat. Off. . |
| 0115388 | 8/1984 | European Pat. Off. . |
| 2595237 | 9/1987 | France . |

Primary Examiner—Max Hindenburg
Attorney, Agent, or Firm—Young & Thompson

[57] ABSTRACT

A blood sampling device in the form of a small manually operated pricker has a barrel (7,21) in which a lancet (1) is captive with a spring (17,22). Partly embracing the barrel is a C-section sleeve (12,30) with a projection (16,35) extending through a slot (10,25) in the barrel to engage the lancet. Initially the lancet is in a forward position with its tip (4) slightly retracted and the spring relaxed, and to prime the device the sleeve is slid to the rear, taking the lancet with it and energising the spring. The lancet may be held there by its tail (1A) being gripped by the barrel (7) while the sleeve (12) is irreversibly deformed or broken by a formation (11) on the barrel and then discarded. The lancet is subsequently released to prick by pressing the tail (1A). Alternatively, the sleeve (30) may be trapped at the rearward position and the lancet released by a trigger (32) on the sleeve withdrawing the projection (35).

11 Claims, 3 Drawing Sheets

DISPOSABLE LANCET DEVICE

This invention relates to blood sampling devices, and in particular to a pricker to draw a small drop of blood for analysis. Such prickers are widely used by diabetics, for example, who need to know their sugar level. However, there are many other applications.

These days, with AIDS, there is widespread concern surrounding the use of needles and their part in transmitting disease. Once a needle has been used on an infected person, subsequent use or an accidental prick on another could be fatal.

There is therefore a growing demand for a pricker which can be used just once and, having been used, be rendered safe for carriage and disposal. It is the aim of this invention to provide such an instrument.

It would also be advantageous to use known and established products as far as possible, and in particular a lancet of a type we provide for a pricker sold under the Registered Trade Mark AUTOLET.

According to the present invention there is provided a disposable pricker comprising a barrel, a spring-loaded lancet carried therein, the lancet tip normally being in a withdrawn position but on energisation and release of the spring means having a momentary projecting position, and a spring priming element captive to the barrel in a forward position and having an engagement with the lancet which is releasable in a rearward position, the priming element being shiftable from its forward to its rearward position to move the lancet to a fully retracted position energising the spring means and there to be deformable to release the lancet and to render the pricker non-reusable after such release.

Conveniently, the lancet is of elongated form with a set of annular ribs between two of which a portion of the spring priming element engages. The spring loading may then be a coil spring acting between the rearmost rib and an abutment at the rear end of the barrel. This rear end will preferably not be closed but formed with a restricted aperture.

The priming element is conveniently a substantially C-section sleeve with a snap fit over the barrel and having a projection which extends through a longitudinal slot in the barrel to engage the lancet. Thus as the priming element is moved rearwardly, the lancet has to follow.

In one form, the co-operation of the sleeve with the barrel is such that, as the sleeve reaches its rearward position, it is irreversibly distorted or broken, allowing it to be discarded. The lancet may then be temporarily retained in its fully retracted position by an end portion projecting through the rear end of the barrel with a tight fit. To release the lancet and make a prick, this projecting end portion is pressed until it snaps free of the barrel end.

Alternatively, the co-operation of the sleeve with the barrel is such that, as the sleeve reaches its rearward position it is irreversibly trapped there. The projection may then be part of a trigger which can be actuated to release the lancet. Preferably, the barrel will be provided with an abutment which prevents actuation of the trigger in the forward position of the sleeve. The sleeve may be retained by hooked formations engaging under lateral ribs on the barrel, and these ribs may have flared portions terminating in shoulders Thus as the sleeve is moved to the rearward position it is distended and then trapped in a ratchet-like manner as it contacts after passing the shoulders. The barrel may have an abutment to stop the sleeve at its rearward position.

Conveniently, the trigger and sleeve will be integrally moulded in a plastics material that allows the trigger movement by flexure of an integral connection between the trigger and the sleeve.

The barrel will have a closure member at its forward end with an opening through which the lancet tip will momentarily project. The lancet tip may initially be shielded by a protective cap which, by abutment with the closure member, prevents retraction of the lancet. However, before use, it can be broken off from the main body of the lancet to allow retraction.

For a better understanding of the invention, one embodiment will now be described, by way of example, with reference to the accompanying drawing, in which.

Figure 1:
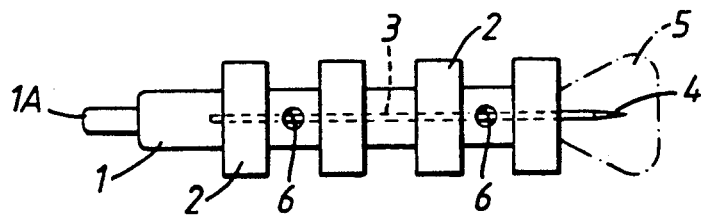
FIG. 1 is a side view of a lancet for a disposable pricker.
Figure 5:
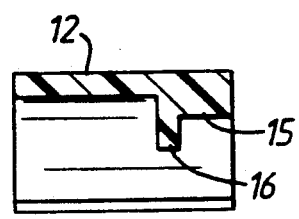
Figure 6:
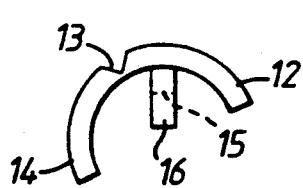
Figure 8:
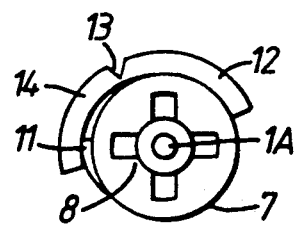
Figure 7:
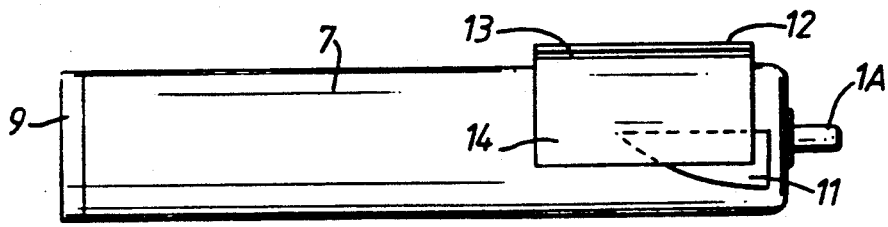
Figure 9:
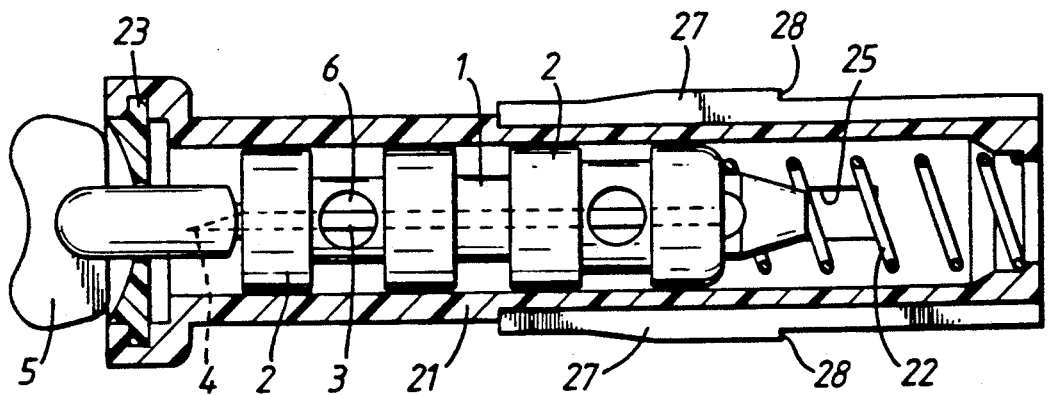
Figure 10:
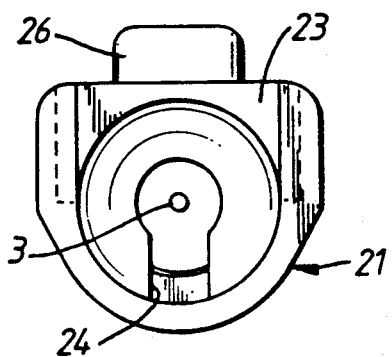
Figure 11:
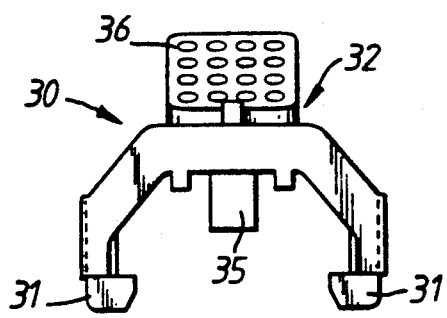
Figure 12:
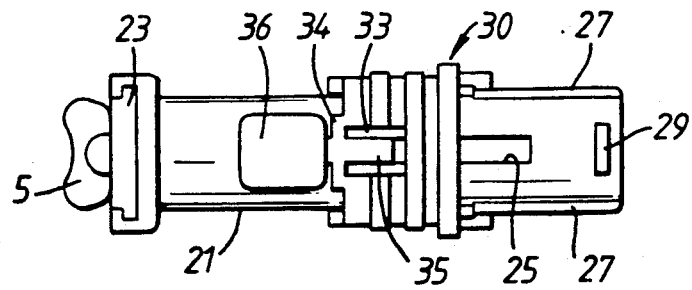
Figure 12:
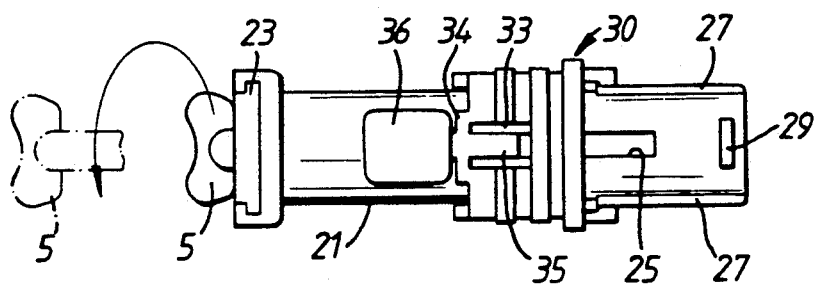
Figure 12:
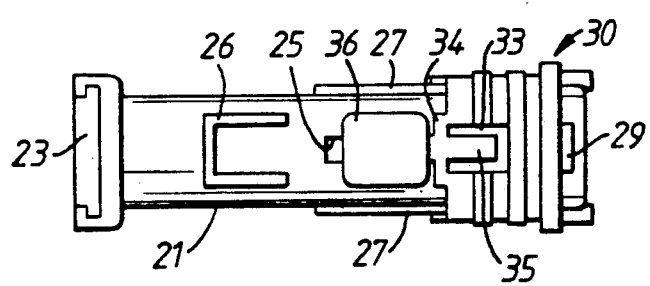
Figure 12:
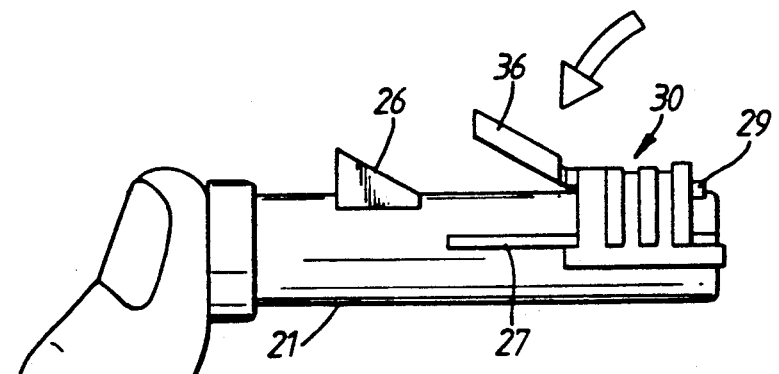

FIG. 5 is a longitudinal section of a priming element that fits the body and engages the lancet, FIG. 6 is an end view of the element of FIG. 5, FIG. 7 is a side view of the pricker as it reaches the fully primed condition, FIG. 8 is a rear end view of the pricker as seen in FIG. 7, FIG. 9 is a longitudinal section through a partly assembled modified pricker, with a lancet similar though not identical to that of FIG. 1, FIG. 10 is a forward end view of the pricker of FIG. 9, FIG. 11 is an end view of a priming element for the pricker of FIG. 9, and FIG. 12(a)–(d) shows the sequence of operations for using the pricker of FIG. 9.

FIG. 1 shows a lancet of known construction suitable for use in this device. It has a moulded plastics body 1 resembling the spool of a spool valve, with several annular ribs 2 and a reduced diameter tail 1A. It coaxially encases a needle 3 whose tip 4 is initially shielded and maintained in a sterile condition by a cap 5 moulded with the body 1 but capable of being broken away. Between some of the ribs there are radial holes 6 exposing the needle 3; they are formed as an incidental part of the manufacturing process, but one of them can now serve a useful purpose as described below.

Figure 2:
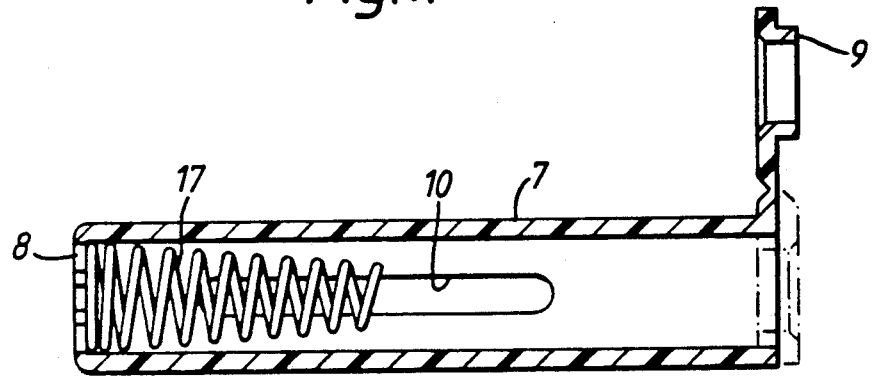
FIG. 2 is a longitudinal section of the main body of the pricker.
Figure 3:
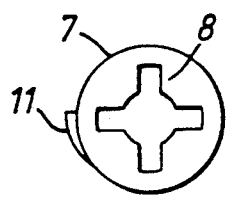
FIG. 3 is a rear end view of the body of FIG. 2.
Figure 4:
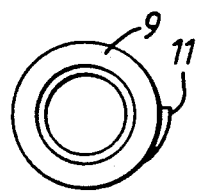
FIG. 4 is a forward end view of the body of FIG. 2.

The lancet is a loose sliding fit in a cylindrical barrel 7, also of moulded plastics material. At one end (the rear end) the barrel is partially closed by equispaced lugs 8 projecting inwardly to leave a clear circular aperture of a diameter marginally smaller than that of the unribbed portions of the lancet body 1 but greater than that of the tail 1A. The lugs 8 will have a certain flexibility and resilience. At the other, forward end the barrel is partially closable by a ring 9 moulded integrally with it and initially being in the full line position of FIG. 2. It is attached by a thin web which allows it to be hinged through 180° to snap into the end of the cylinder. Its outer face in this position presents a countersunk hole into which a finger or thumb is pressed for pricking.

Intermediate the ends of the barrel 7 is a longitudinal slot 10. In this example it is shown as straight and parallel to the axis, but it could be helical to generate a twisting action, which might be more effective or make the device easier to use. Towards the rear of the barrel there is an angled protrusion 11 on one side of the projected line of the slot 10, and its function is described below.

A further component of the device is a priming sleeve 12. This is not a complete sleeve, but rather a C-shaped member which can closely embrace the barrel 7. It is made of moulded plastics and can be snapped on laterally. The arc of the C is therefore greater than 180°, but there is a line of weakness 13 parallel to the axis and at a position that, with the edge remotest from it, subtends an angle less than 180° at the axis. Thus, when the wing 14 beyond the line 13 breaks off, the remainder of the sleeve can no longer grip and remain on the barrel. Also integrally moulded as part of the sleeve is a central, inwardly projecting lug 15 whose root can slide within the slot 10 and whose tip 16 can engage between the ribs 2 of the lancet body 1 and into one of the holes 6.

A fourth component is a coil spring 17 of conical form which fits within the barrel 7 and which surrounds the rear end of the lancet body 1. The smaller end of this spring is forward and abuts the rearmost rib 2, at the same time gripping around the body 1. Conveniently, it is so arranged before insertion into the barrel 7. With the ring 9 in the clear, full line position of FIG. 2, the spring/lancet assembly is inserted at the forward end of the barrel 7, the larger end of the spring first, and is urged in until the spring abuts the lugs 8. The larger end of the spring is an interference fit in the barrel 7 so that, with the grip exerted by the smaller end on the body 1, the lancet is captive.

The sleeve 12 is then snapped on with the lug 15 engaging through the forward end of the slot 10 and with its tip 16 in one of the holes 6. The ring 9 is snapped over to the dotted line position, making the device complete, but not immediately ready for use. In order to clear the cap 5, which will preferably be flat or spade-like, the ring 9 may have a slot opposite the hinge. A smaller cap 5 is possible, but not so convenient to use.

To prime the device, the cap 5 is twisted off, the lancet being held against rotation and re-extraction by the lug 15. The sleeve 12 is then slid back, causing the lancet to be withdrawn and compressing the spring 17. The tail 1A of the lancet body 1 passes freely through the aperture formed by the lugs 8 but once the shoulder at the root of the tail arrives at the aperture the lugs exert a grip to retain the lancet retracted. At the same time the sleeve is engaged by the protrusion 11 and is distorted more than it was when snapped on in the first place. This places additional strain on the line of weakness 13 and the wing 14 breaks away, leaving the rest of the sleeve 12 free but not usable again. It is therefore thrown away.

To prick a finger or thumb, the ring 9 is placed over the desired spot and the tail 1A of the lancet is pressed. As the shoulder at its root clears the lugs 8, the spring 17 shoots the lancet forward to effect the prick and, since the spring is anchored, it retracts the lancet immediately just enough to leave the device safe. But without a sleeve it is useless, so it too is discarded after this single use.

Rather than gripping the body 1 by the smaller end of the coil, the latter could have a short length turned radially inwards at that end, to engage in the rearmost hole 6. However, that involves more complicated manufacture and assembly and probably will not be preferred. Also, instead of relying on an interference fit of the larger end of the spring, it may be anchored by embedding the final turn in the plastics material of the barrel, which can be locally heated to soften the material and make it receptive.

Referring now to FIGS. 9 to 12, a modified version uses a generally similar lancet, although it does not have an extended stepped tail 1A, and the geometry of the cap is slightly different. It is shown in FIG. 9 and referenced similarly to the lancet of FIG. 1.

Again, it is a loose sliding fit in a barrel 21, and between its rearmost rib and the rear, partially closed end of the barrel there is a coil spring 22. On assembly, it is trapped by a slot-in plate 23 at the leading end or mouth of the barrel, the plate having a cutout portion 24 to embrace the forward end of the lancet 1 around the stem of the protective cap 5 and in front of the leading rib 2.

The barrel has a longitudinal slot 25, as before, and externally at the forward end of this there is an inclined pad 26. Symmetrically on either side of the slot, and on diametrically opposite sides of the barrel, there are projecting ribs 27, which flare outwardly over intermediate portions terminating at shoulders 28. At the extreme rear end of the barrel, aligned with the slot 25, there is a projecting lug 29.

A priming sleeve 30 performs the same function as the sleeve 12, but operates in a different manner. It partly embraces the barrel and at its extremities it has inwardly projecting lugs 31 which engage under the lateral ribs 27 to retain the sleeve to the barrel, although allowing longitudinal movement limited by the slot 25, the pad 26 and the lug 29. The sleeve 30 has an integrally formed trigger 32. Its central portion has a U-shaped cutout 33 whose mouth is spanned by a slender bar 34 which forms a hinge pin for the trigger. To the rear of the bar 34 a hooked finger 35 within the cutout points down through the slot 25 to engage between the ribs 2 of the lancet. On the forward side of the hinge pin 34, there is a tab 36 inclining away from the barrel at an angle corresponding to the slope of the pad 26.

When first assembled as shown in FIG. 12(a), the priming sleeve 30 is at its forward position with the tab 36 lying over the pad 26 and therefore being incapable of being pressed down. Thus the hooked finger 35 is trapped between the lancet ribs 2. The sleeve 30 cannot move backwards while the cap 5 is still on the tip of the lancet 1. But when it is to be used, the cap 5 is twisted off (FIG. 12(b)), and then the sleeve 30 is slid to the rear end of the barrel (FIG. 12(c)) until it comes up against the lug 29. As it does so, the arms of the sleeve which have been forced out by the flared portions of the ribs 27 snap inwards as they come clear of the shoulders 28. Thus, the sleeve is trapped in a ratchet-like manner at its rearmost position, the lancet is fully retracted, and the spring 22 is fully compressed. The instrument is then held over the area to be pricked, and the user presses the tab 36 (FIG. 12(d)) which causes the hooked finger 35 to hinge clear of the lancet ribs. The lancet 1 then shoots forward, makes its prick, and then immediately withdraws within the cylinder. There, it is inaccessible, and since the sleeve 30 is trapped, reinstatement to the original starting position is not possible.

We claim:

1. A disposable pricker comprising a barrel, a lancet carried therein and having a tip pointing towards the forward end of the barrel, spring means acting between the barrel and the lancet, the lancet normally being in a withdrawn position but on energisation and release of the spring means attaining a position in which the tip momentarily projects beyond said forward end of the barrel, and a spring priming element captive to the barrel in a forward position and having an engagement with the lancet which is releasable in a rearward position, the priming element being shiftable from its forward to its rearward position to move the lancet to a fully retracted position energising and enabling release of the spring means and being rendered by its co-operation with the barrel at the rearward position incapable of being restored to its forward position, thereby making the pricker usable once only.

2. A pricker as claimed in claim 1, wherein the lancet has annular ribs between two of which a portion of the spring priming element engages.

3. A pricker as claimed in claim 2, wherein the spring means is a coil spring acting between the rearmost rib and an abutment at the rear end of the barrel.

4. A pricker as claimed in claim 1, wherein the priming element is a sleeve which partially embraces and snap fits laterally over the barrel and which has a projection extending through a longitudinal slot in the barrel to engage the lancet.

5. A pricker as claimed in claim 4, wherein the barrel has a formation at its rear end which, as the sleeve reaches its rearward position, irreversibly distorts or breaks the sleeve, allowing the sleeve to be discarded, and wherein the lancet is then temporarily retained, in its fully retracted position by an end portion of the lancet projecting through the rear end of the barrel with a tight fit.

6. A pricker as claimed in claim 4, wherein the barrel has a formation which, as the sleeve reaches its rearward position, irreversibly traps the sleeve there, and wherein the projection is part of a trigger which can then be actuated to release the lancet.

7. A pricker as claimed in claim 6, wherein the barrel is provided with an abutment which prevents actuation of the trigger in the forward position of the sleeve.

8. A pricker as claimed in claim 6, wherein the sleeve is retained by hooked formations engaging under lateral ribs on the barrel, and wherein the ribs have flared portions terminating in shoulders which, as the sleeve is moved to the rearward position, distend the sleeve and then trap it in a ratchet-like manner as the sleeve contracts after passing the shoulders.

9. A pricker as claimed in claim 6, wherein the barrel has an abutment to stop the sleeve at the rearward position of said sleeve.

10. A pricker as claimed in claim 6, wherein the trigger and the sleeve are integrally moulded in a plastics material that allows the trigger movement by flexure of an integral connection between the trigger and the sleeve.

11. A pricker as claimed in claim 6, wherein the barrel has a closure member at its forward end with an opening through which opening the lancet tip will momentarily project, and wherein the lancet tip is initially shielded by a protective cap which, by abutment with the closure member, prevents retraction of the lancet, but which can be broken off from the main body of the lancet to allow retraction.

* * * * *